US008197491B2

(12) United States Patent
Kerr et al.

(10) Patent No.: US 8,197,491 B2
(45) Date of Patent: Jun. 12, 2012

(54) INJECTABLE FASTENER SYSTEM AND METHOD

(75) Inventors: Sean Kerr, Oreland, PA (US); Edward August Kurek, III, Lansdale, PA (US); Junior Julien, Wayne, PA (US)

(73) Assignee: Synthes USA, LLC, West Chester, PA (US)

( * ) Notice: Subject to any disclaimer, the term of this patent is extended or adjusted under 35 U.S.C. 154(b) by 1178 days.

(21) Appl. No.: 11/959,675

(22) Filed: Dec. 19, 2007

(65) Prior Publication Data

US 2008/0167658 A1 Jul. 10, 2008

Related U.S. Application Data

(60) Provisional application No. 60/870,757, filed on Dec. 19, 2006.

(51) Int. Cl.
*A61B 17/58* (2006.01)
*A61B 17/60* (2006.01)
*A61F 2/00* (2006.01)

(52) U.S. Cl. ............................................. 606/93; 606/92
(58) Field of Classification Search ............... 606/92–95, 606/331, 76–78; 433/32
See application file for complete search history.

(56) References Cited

U.S. PATENT DOCUMENTS

| 4,033,484 | A | 7/1977 | Ornsteen |
| 5,026,187 | A | 6/1991 | Belanger et al. |
| 5,720,753 | A | 2/1998 | Sander et al. |
| 5,988,445 | A | 11/1999 | Massena |
| 6,080,161 | A | 6/2000 | Eaves, III et al. |
| 6,241,734 | B1 * | 6/2001 | Scribner et al. ................. 606/93 |
| 6,248,110 | B1 * | 6/2001 | Reiley et al. .................... 606/93 |
| 6,413,278 | B1 * | 7/2002 | Marchosky ................ 623/17.16 |
| 6,436,143 | B1 * | 8/2002 | Ross et al. ................. 623/17.16 |
| 6,527,772 | B2 | 3/2003 | Enayati |
| 6,610,079 | B1 | 8/2003 | Li et al. |
| 6,623,487 | B1 | 9/2003 | Goshert |
| 6,676,664 | B1 * | 1/2004 | Al-Assir ......................... 606/94 |
| 6,989,012 | B2 | 1/2006 | LeHuec et al. |
| 7,104,994 | B1 | 9/2006 | Amis et al. |
| 2004/0030342 | A1 | 2/2004 | Trieu et al. |
| 2007/0233148 | A1 * | 10/2007 | Truckai et al. .................. 606/92 |

FOREIGN PATENT DOCUMENTS

| DE | 10323810 | 11/2004 |
| GB | 992573 | 5/1965 |
| JP | 03-085179 | 4/1991 |
| JP | 04-221538 | 8/1992 |

(Continued)

OTHER PUBLICATIONS

"European Patent Application No. 04750971.6, Communication mailed Jun. 12, 2008", 5 pgs.

(Continued)

*Primary Examiner* — Thomas C. Barrett
*Assistant Examiner* — Melissa A Golob
(74) *Attorney, Agent, or Firm* — Morgan Lewis & Bockius LLP

(57) ABSTRACT

Methods and devices are shown for forming polymer fasteners into bone by expelling the polymer from a cannula. Devices and methods shown allow a user to form multiple fasteners of various sizes without re-loading a device. Devices and methods shown further provide temperature profiles during fastener formation that reduce or eliminate thermal necrosis. Devices and methods shown further provide fasteners with increased strength.

16 Claims, 4 Drawing Sheets

FOREIGN PATENT DOCUMENTS

| | | |
|---|---|---|
| JP | 07-313586 | 12/1995 |
| JP | 08-024347 | 1/1996 |
| JP | 09-201330 | 8/1997 |
| WO | WO-01/32100 A2 | 5/2001 |

OTHER PUBLICATIONS

"Japanese Application No. 2002-506661, Notice of the Reason for the Rejection mailed Feb. 27, 2008", (w/English Translation), 7 pgs.

"Japanese Application No. 2002-506661, Official Notice of Reason for the Final Rejection mailed Jul. 11, 2008", (w/English Translation), 4 pgs.

Kaneko, Y., et al., "Synthesis and Swelling—deswelling kinetics of poly(N-isopropylacrylamide) hydrogels grafted with LCST modulated polymers", *Journal of Biomaterials Science, Polymer Edition*, 10(11), (1999), 1079-1091.

Stile, R. A., et al., "Synthesis and Characterization of Injectable Poly(N-isopropylacrylamide)-Based Hydrogels That Support Tissue Formation in Vitro", *Macromolecules*, 32, (1999), 7370-7379.

\* cited by examiner

INJECTABLE FASTENER SYSTEM AND METHOD

RELATED APPLICATION

This patent application claims the priority benefit of U.S. Provisional Patent Application Ser. No. 60/870,757 filed Dec. 19, 2006 and entitled "INJECTABLE FASTENER SYSTEM", which application is incorporated herein by reference.

BACKGROUND

The present invention relates to methods for attaching plates to bone. Specific examples include attaching bioresorbable plates to bone using bioresorbable fasteners.

One current methods for attaching bioresorbable plates to bone fragments is bioresorbable screws inserted with a screwdriver either manually or powered. In order to insert a screw, a threaded hole must be made into the bone. Threading or tapping is very technique sensitive and if done incorrectly the screw will not properly hold the plate to the bone. In addition, using a manual screwdriver can cause surgeon fatigue if the case requires more than a few screws to be inserted. Using a powered screwdriver speeds insertion and reduces surgeon fatigue, but can strip screws or torque off the screw head if not handled properly. The strength of standard bioresorbable screws is also in need of improvement, particularly for load bearing applications. Methods to improve the strength of resorbable screws through drawing exist, but require additional manufacturing processes and require that each screw is individually machined which is more time consuming than injection molding of standard screws. Even with these processes, the shear strength of a screw is diminished since only the minor root diameter of the threads impart the load carrying capacity. A screw that is marketed as 1.5 diameter actually only has the strength of a 1.1 diameter pin since the threads do not impart strength, but only pull out resistance.

Another method for attaching plates is using tacks or rivets. Inserting a tack is very technique sensitive. If the hole is drilled slightly oversized, a tack will not have sufficient holding power. Even if the hole is of the proper size, a tack generally does not have the same pull out resistance as screws since no threads are formed into the bone.

Eaves et al in U.S. Pat. No. 6,080,161 describe a cannulated pin that is inserted into a hole, heated and deformed in place. This method obviates the need to tap the hole and provides a means to accommodate slight variations in the diameter of the hole that is drilled. However each fastener must be individually heated adding additional time to the operative procedure. Also, the heat required to deform the fastener can add the risk of thermal necrosis to the surrounding tissue.

A relatively new method of fastener insertion is an ultrasonically inserted pin inserted using a sonotrode. This method is relatively simple, does not require tapping and requires only a minimal amount of training. The high temperatures created during insertion may induce thermal necrosis. This risk is especially pronounced at the interface of the polymer and the bone since this is where the heat is generated during insertion. Also, the molten polymer can be extruded under the plate and away from the hole during insertion since the hole that is drilled is smaller than the diameter of the fastener. Also, the fastener will often melt to the plate making removal of one individual fastener from the plate difficult.

In all of the above listed methods, the instrument must be reloaded after each fastener is inserted. This can be a time consuming process and the fastener is at times unintentionally disengaged from the instrument during this handling process. In addition, multiple lengths and diameters of fasteners must be on hand to complete each case. These fasteners are packaged in bulky packages and significant space is required to house this inventory.

A need exists for an improved fastener and method that addresses these and other concerns.

DETAILED DESCRIPTION

Figure 1:
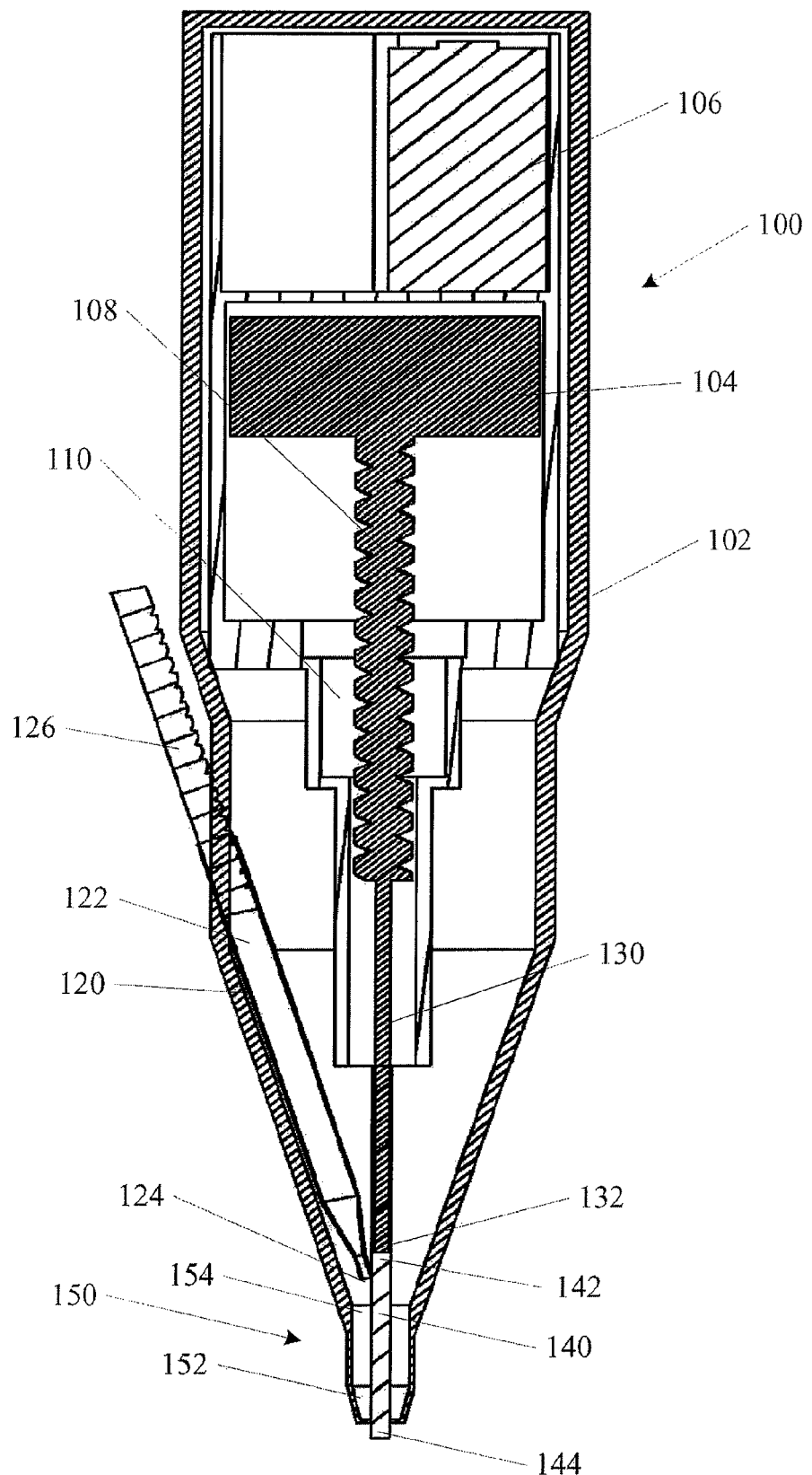
FIG. 1 is a cross section of an example bone support attachment device according to an embodiment of the invention.

In the following detailed description, reference is made to the accompanying drawings which form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and minor deviations may be made without departing from the scope of the present invention.

FIG. 1 shows an example of a bone support attachment device 100. In one embodiment, an amount of polymer is heated to a temperature to provide desired properties such as a temperature high enough to flow, and low enough to limit or prevent necrosis of tissue. The flowable polymer is expelled from an end of the bone support attachment device 100, and hardens in place to form a bone fastener. In one embodiment, the polymer includes a bioresorbable polymer. Selected details and advantages are discussed in more detail below.

A body 102 forms the structure of the bone support attachment device 100. At one end of the device 100 is located an injection cannula 140. A plunger 130 is configured to pass through the injection cannula 140 and expel an amount of polymer from the injection cannula 140. The plunger 130 shown in the embodiment of FIG. 1 enters the injection cannula at a first end 142 of the injection cannula 140, which in turn expels an amount of polymer from a second end 144 of the injection cannula 140.

In one embodiment, the plunger is driven with respect to the cannula using a motor 104. One example of a plunger driving system includes a threaded member 108 coupled to the motor 104, although the invention is not so limited. Other examples of plunger driving systems include, but are not limited to manual operation, pneumatic operation, a controlled chemical reaction or explosion.

A battery 106 is illustrated in FIG. 1 to power aspects of the bone support attachment device 100, including the motor 104. One example of a battery 106 includes a lithium ion battery. Other battery examples include nicad, alkaline, lead acid and nickel metal hydride. The batteries 106 can either be of the disposable or rechargeable type. In alternate embodiments the power source is an AC to DC power supply that energizes the motor via a cable.

A polymer supply inlet 124 is shown coupled to a side of the injection cannula 140. In operation, when a tip 132 of the plunger 130 travels from the first end 142 toward the second end 144 of the injection cannula 140, the supply inlet 124 is cut off as the tip 132 passes by. When the tip 132 is returned to the first end 142 of the injection cannula, the supply inlet 124 is again exposed and available to refill the injection cannula 140.

In one embodiment, a chamber 120 is included to house a block of polymer. In one example the chamber 120 includes a cannula, or other cylindrical chamber, although the invention is not so limited. FIG. 1 shows a block of polymer 122 located within the chamber 120. Using a chamber, and a supply of polymer 122, multiple fasteners can be formed without reloading the bone support attachment device 100. Additionally, fasteners of varying dimensions can be formed from a single polymer supply. For example a fastener with a larger diameter for additional strength, or a fastener with a longer length to accommodate a thicker bone support plate can be formed.

To form multiple fasteners, fasteners of varying dimensions, etc., the plunger 130 is withdrawn into a selected location within the injection cannula 140. Heated polymer is flowed into the injection cannula 140 through the polymer supply inlet 124. In one embodiment a local region of the chamber 120 near the inlet 124 is heated to a sufficient temperature to flow the polymer. A mechanical feed system, manual feed, or other system provides pressure to inject the liquid polymer at the inlet 124 into the injection cannula 140.

In one embodiment, a starting position of the tip 132 of the plunger 130 is varied to adjust a volume of the injection cannula available for polymer. The flowing polymer will fill the size hole as will be described in more detail below, while the volume of polymer necessary to form the fastener is selected by moving the starting location of the tip 132.

In an alternate embodiment, the volume of material that is transferred into the injection cannula 140 is controlled by the displacement of cartridge plunger 126. The displacement of this cartridge can be controlled by any means, including, but not limited to a variable displacement mechanism or motor. The means of adjusting the displacement can be user controlled either through a knob, lever, or switch.

In certain procedures, few fasteners are utilized and thus a volume of polymer that can delivery approximately 5 fasteners may be sufficient. In other cases, such as in a craniosynostosis case, more than 150 fasteners may be utilized. In these cases a volume of polymer that could deliver 20 or more fasteners would be beneficial to reduce the number of times that the cartridge needs to be replaced during the procedure. The number of fasteners that can be delivered from each chamber 120 is dependent on the volume of the final fastener and the volume of polymer within the chamber 120.

The diameter of the chamber 120 can be modified to suit the requirements for size, heat transfer, the size of fastener desired and the number of fasteners per cartridge. In the preferred embodiment, the chamber diameter is between 2 and 4 mm and is between 30 and 50 mm long to deliver up to approximately 20 fasteners. However, invention is not so limited.

In one embodiment, the polymer 122 is heated within at least a portion of the chamber 120. It is desirable to heat the polymer to a temperature where the polymer flows, but at a temperature that is not so high as to cause necrosis of tissue.

In one example the polymer 122 is substantially non-flowable at room temperature or physiological temperatures (i.e. 15-37° C.). The polymer 122 or portions of the polymer are heated to a temperature of at least the glass transition temperature ($T_g$), where the material is rendered sufficiently flowable to be expelled from the chamber 120. In one embodiment, the polymer 122 and chamber 120 are coordinated together as a cartridge. In other embodiments, the polymer 122 is refillable by itself, and inserted into a chamber 120 that is part of the bone support attachment device 100.

For one example bioresorbable polymer, the $T_g$ is approximately 55° C. While this describes the minimum temperature required to be render the material at least partially flowable, it may be advantageous to increase the temperature to a temperature up to or even above the melting point of the polymer to reduce the force required to expel the material from the injection cannula 140. In one embodiment this temperature is between 130 and 180° C., but temperatures between 50 and 250° C. could be utilized. It is, however, advantageous not to excessively heat the polymer 122. Excessive heat will degrade the polymer, consume additional power from the internal power source, heat the instrument itself and create an injected polymer that can cause thermal necrosis.

In certain embodiments, the temperature of the polymer 122 within the chamber 120 may not be homogeneous, but rather incorporate a gradient from a higher temperature adjacent to the polymer supply inlet 124 to a lower temperature where polymer flow is not necessary. This gradient can be incorporated to optimize the expulsion force while minimizing the issues associated with excessive heat in the polymer addressed above. Certain embodiments may only actively heat the region adjacent to the polymer supply inlet 124 to provide this gradient.

The method of producing heat in the preferred embodiment is through electrically resistive elements that are powered by the battery or batteries 106. Materials that these electrically resistive elements can be manufactured from include, but are not limited to, nickel chromium wire, conductive plastics, ceramics, quartz, etc. In alternative embodiments, the methods of producing heat may include, but are not limited to, induction, radio frequency, vibrational, ultrasonic, microwave, frictional, exothermic chemical reactions and infrared. The temperature can either be controlled actively or passively. Any known method of active temperature control could be utilized including sensing the temperature through a temperature sensor and utilizing this to control the amount of power going to the heater. Resistive heating elements that have a resistance that increases with increasing temperature (positive temperature coefficient or PTC) can provide a means of self regulating their temperature actively without additional controls. In alternate embodiments the temperature is controlled passively without active regulation.

In one embodiment, the polymer includes a thermoplastic polymer 122. On example of a thermoplastic polymer includes a bioresorbable aliphatic polyester. Aliphatic polyesters that can be used in this device include, but are not limited to, homo- and co-polymers of polylactic acid, polyglycolic acid and polycaprolactone. These polymers have been used for a number of years in orthopedic devices and are generally regarded as biocompatible and bioresorbable. In the preferred embodiment the polymer is substantially non-crystalline, but at least partially crystalline polymers could be used. Other biocompatible but non-resorbable polymers could be used in instances where the resorbability was undesirable. Non-resorbable polymers that could be used include, but are not limited to, acrylic, polycarbonate, PEEK, polypropylene, and polyethylene.

In one embodiment, the thermoplastic polymer 122 is compounded with an agent to increase radiopacity, osteoconductivity, osteoinductivity or deliver a therapeutic agent. Possible radiopacifiers include, but are not limited to, barium sulfate, zirconium oxide, titanium oxide, titanium dioxide, calcium, tantillum and iodine. Agents to increase osteoconductivity include, but are not limited to, hydroxyapatite, calcium phosphate and calcium sulfate. Agents to increase osteoinductivity include, but are not limited to, bone morphogenic proteins and growth factors. Therapeutic agents include, but are limited to, antibiotics, antiseptics, analgesics, chemotherapeutics, and pain medications.

As mentioned above, in one embodiment the chamber 120 and polymer 122 are coordinated together as a replaceable cartridge. This configuration provides a disposable delivery vessel for the polymer to obviate the need to clean the internal mechanisms and chambers of the injection device. One example chamber 120 in a cartridge embodiment is constructed of a heat resistance metal such as stainless steel or aluminum or of a heat resistant, biocompatible polymer such as PEEK, polysulphone, Radel, or polycarbonate.

In selected polymer cartridge embodiments, the cartridge further includes a cartridge plunger 126 that expels the polymer when advanced. In one embodiment the cartridge plunger 126 is integral to the polymer cartridge and is disposed of along with the polymer cartridge. In alternative embodiments, the cartridge plunger 126 is a part of the bone support attachment device 100 and separated by a seal from the polymer 122. The advancement of the cartridge plunger 126 is controlled by the bone support attachment device 100 as described in more detail below.

In an alternate embodiment the polymer 122 is provided in discrete sections that are not heated in the chamber 120. The volume of each section would correspond to the desired volume of each fastener. In this embodiment the unheated sections are individually transferred to the injection cannula through a mechanism, or manually. They are then individually heated in the injection cannula 140. In one embodiment, they are stacked in a linear or circular array. Alternately, they could be transferred individually into the injection cannula by the user without the aid of an internal mechanism or cartridge.

In one embodiment, one or more heating elements are provided at a tip region 150 surrounding the injection cannula 140. The heating elements in the tip region provide further control of the polymer temperature as it comes into contact with tissue and forms a fastener.

In one embodiment the injection cannula 140 is actively heated in the entire region from the first end 142 to the second end 144. In one embodiment at least part of the heat for the injection cannula is generated through an actively regulated heater in order to maintain consistent temperatures. Once the cannula exits the distal tip, it is exposed to variable thermal conditions (i.e. dry bone, wet bone, room temperature, physiological temperature). Active temperature regulation will help to maintain a consistent temperature profile in the cannula. In one embodiment, a thermal gradient is provided in the injection cannula 140 where the polymer 122 is at a higher temperature in a proximal region 154 of the tip than at a distal end 152 of the tip 150. The higher temperature at the proximal end 154 facilitates improved flow characteristics, while the lower and more tightly controlled temperature at the distal end 152 reduces the possibility of necrosis in tissue. In one embodiment, multiple heating elements and/or thermal control circuits are used to control the temperature gradient.

Figure 2:
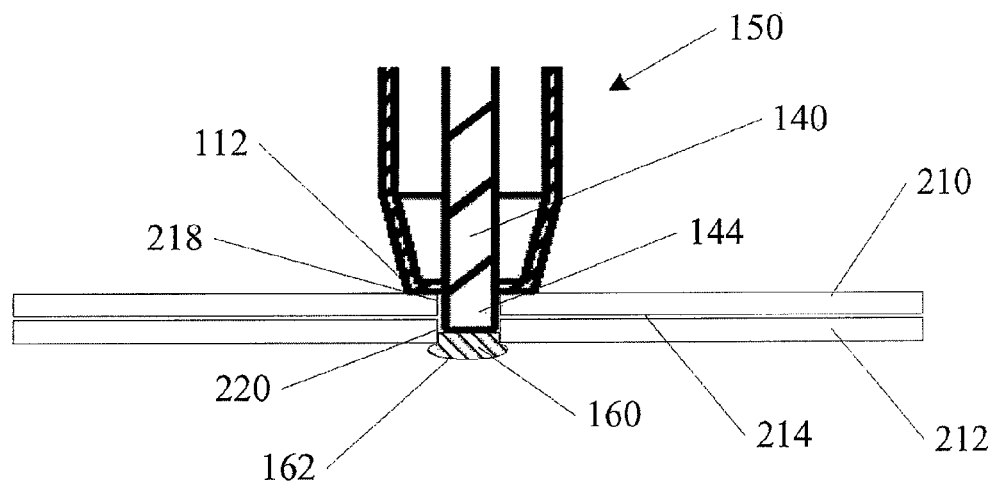
FIG. 2 illustrates a stage in a fastening operation according to an embodiment of the invention.

FIG. 2 shows a close of view of the tip 150 of the bone support attachment device 100 during formation of a fastener. A cross section view of a bone support structure 210 is shown located adjacent to a portion of bone 212. A hole 218 is included through the bone support structure 210 and a corresponding hole 220 is included in the bone 212.

In one embodiment, the bone support structure 210 includes a plate, although other forms of support structures are within the scope of the invention. In one embodiment, the bone support structure 210 is formed from a bioresorbable material such as a bioresorbable polymer. In one example, the bone 212 is a thin layer of bone, such as a portion of a skull, although the invention is not so limited. An interface 214 is formed between the bone support structure 210 and the bone 212. As shown in the Figure, frequently a gap is included at the interface 214.

In one embodiment, a depth gauge 112 is included near the tip 150 of the bone support attachment device 100. An example of a depth gauge includes a static shelf that butts against the bone support structure 210 and limits a depth that the injection cannula 140 travels within the holes 218 and 220. The depth gauge 112 determines where in the holes 218 and 220 the second end 144 of the injection cannula 140 is located. In one embodiment, the desired depth of the second end 144 is through the hole 218 in the bone support structure 210, past the interface 214 and partially into the hole 220 in the bone. By passing the interface with the second end 144, a possibility of polymer being extruded into a gap at the interface 214 is reduced or eliminated.

Extrusion of polymer between any gap at the interface is undesirable for a number of reasons. Any polymer that is accidentally extruded at the interface is not available to form structural portions of the fastener, therefore strength of the fastener is lessened by extrusion into a gap at the interface. Further, any extrusion at the interface tends to open any existing gap further.

In one embodiment, the depth gauge 112 is dynamic. For example, in one embodiment, once a predetermined volume of polymer is extruded into the holes 218, 220, the depth gauge is moved to retract the second end 144 of the injection cannula 140 from the holes 218, 220.

In selected embodiments, the position of the depth gauge 112 is user selectable to adapt to plates of various thicknesses and holes of different depths. In one embodiment the depth gauge 112 is larger than the hole 218 or any countersunk area around the hole 218 in the bone support structure 210. This allows the surgeon to compress the bone support structure 210 against the tip 150 against the bone 212. In an alternate embodiment the depth gauge 112 is slideably attached, and the second end 144 of the cannula 140 protrudes only when the instrument is compressed against the bone support structure 210. This feature would protect the second end 144 except when injection is about to take place. In one embodiment the second end 144 of the cannula 140 seals against a portion of the tip 150 so as to not allow extraneous fluid and matter to enter the inside of the injection cannula 140 or between the cannula and tip 150.

In one embodiment, the outer diameter of the second end 144 of the cannula 140 is slightly smaller than the hole 220 in the bone 212. Without implying limitation, this diameter would generally fall within the range of 1.3 to 3.5 mm at the most distal point. This is to allow the cannula 140 to enter the hole 220 in the bone 212 with minor resistance. In one embodiment, the hole 220 in the bone 212 is tapered or stepped to allow for a larger opening for entry of the cannula 140 and a smaller hole to minimize the amount of material required to fill the entire opening.

FIG. 2 further shows a volume of expelled polymer 160. The process of expelling a polymer in contrast to heating in place has an advantage of forming a cooled profile across the volume of expelled polymer 160. A surface 162 of the expelled polymer cools first on contact with tissue or other external surfaces. The interior of the expelled polymer remains flowable, and tends to form a desirable shape similar to blowing up a balloon. The balloon shape helps to form a mechanical bond in the bone 212 similar to a rivet. Additionally, the cooled surface 162 is far less likely to cause thermal necrosis with tissue it comes into contact with. In contrast, for example, polymer that is heated through sonic vibration in a hole in bone is hottest at the interface between the bone and the polymer.

In one embodiment, the plunger 130 has a slight clearance fit relative to the inner walls of the injection cannula 140. The clearance is generally within the range of 2 to 200 μm. The clearance should be small enough as to not allow polymer to flow past the distal tip of the plunger yet large enough as to not create mechanical interference. In one embodiment the plunger 130 rotates as it translates to create additional friction as it travel within the cannula 140. This friction produces heat which reduces the viscosity of any polymer which flows between the cannula 140 and plunger 130. This rotation can be achieved through the attachment of the plunger 130 to the rotating lead screw 108. In one embodiment the clearance is eliminated at the second end 144 of the cannula 140 and an interference fit is achieved. An interference fit helps to sever any polymer from the plunger 130 and cannula 140 at the end of the cycle.

In one embodiment, the entire plunger 130 or at least the distal end of the plunger 130 is manufactured from or coated with a non stick material such as silicone or PTFE. This prevents polymer from adhering to the plunger 130 after a formed fastener is completed.

As discussed above, in one embodiment, the temperature profile of injection cannula 140 is controlled to allow the polymer to remain sufficiently flowable yet not induce thermal necrosis into the bone at the second end 144. Thermal necrosis in living tissue is a complex time and temperature dependent relationship, but is often considered to begin when the tissue reaches 48° C. Additionally, the bone support device 210 or plate may begin to deform under thermal stress. If, for example, a polylactide/polyglycolide polymer is used, a suitable range around a glass transition temperature of 48-55° C. is used for the injection cannula 140.

The rate at which the polymer cools within the cannula is dependent upon the rate at which it travels. Thus a lower temperature of the cannula at the distal end could be permitted if the polymer travels at a high enough rate such that it does not have sufficient time to equilibrate with the temperature of cannula itself.

In one embodiment the tip 150 of the bone support attachment device 100 acts as a heat sink and dissipates the heat from distal portion of the cannula 140 allowing for reduced temperature. This dissipating effect can be optimized through the use of thermally conductive materials and designs to accentuate heat transfer through conduction and convection. Such materials include, but are not limited to, aluminum, aluminum filled polymers, copper, brass, conductive metal, silver, and thermally conductive polymers or ceramics. Designs to promote heat transfer include, but are not limited to fins, vanes, ribs, pins, and spikes, etc. Active cooling could also be incorporated including, but not limited to, syringe irrigation, gases ($N_2$, air or $CO_2$), liquid nitrogen, peltier effect devices, vortex chillers, pumped saline, fans and recirculating chilled liquids. These methods of cooling the second end 144 of the cannula 140 can also be used to cool the polymer head once it has been formed as disclosed below.

Figure 3:
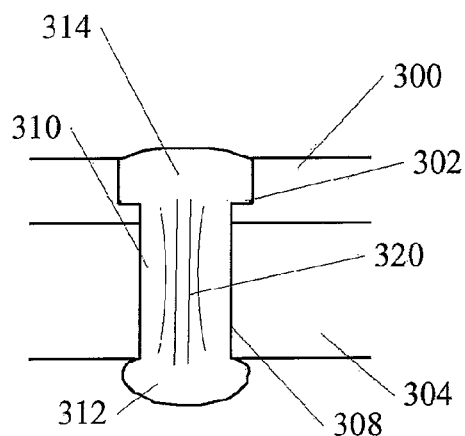
FIG. 3 illustrates another stage in a fastening operation according to an embodiment of the invention.

As the polymer exits the second end 144 of the cannula 140 and into the bone 212, it begins to flow and interdigitate into any pores within the bone 212. FIG. 3 illustrates the flow anticipated when a hole 308 is in relatively non porous material and the hole extends through the bone 304. In this case, the polymer expands on the far cortex and forms a bulbous tip 312 with a diameter larger than the hole created 308. This provides for a rivet-like effect with additional pullout resistance.

FIG. 3 further illustrates a strengthening property that is unique to an extrusion process as described in the present disclosure. During extrusion, through a plate 300 and into bone 320, polymer molecules 320 are stretched and aligned along a long axis of the fastener 310. The alignment of the polymer molecules provides significant increases in fastener strength. In selected embodiments, strength of the fastener is increased by up to at least 75% over non-extruded polymer. A number of process variables such as the temperature at or around the glass transition temperature during extrusion contribute to alignment of polymer molecules.

Figure 4:
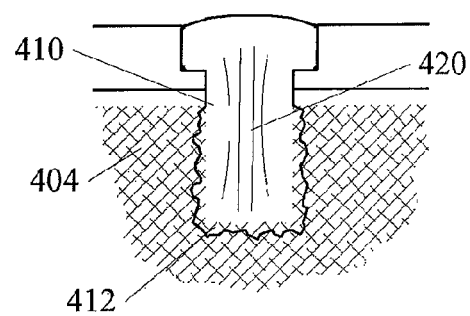
FIG. 4 illustrates another stage in a fastening operation according to an embodiment of the invention.

FIG. 4 illustrates the flow anticipated when a fastener 410 is injected into porous or cancellous bone 404. In this case the polymer can flow into the interstices 412 of the bone 404 and interdigitate with it. This also provides pullout resistance. The embodiment shown in FIG. 4 also illustrates alignment of molecules 420 and strengthening of the fastener 410.

Referring again to FIG. 3, the head 314 that is formed by the fastener is allowed to substantially fill a countersink recess 302 in the plate 300. This provides locking of the fastener 310 to the plate 300 yet allows rotational motion. If locking in rotation is also desired, the countersunk recess can be incorporate grooves or other surface irregularities that the polymer can flow into. The injected polymer and fixation device can also be bonded together if melted.

Figure 5:
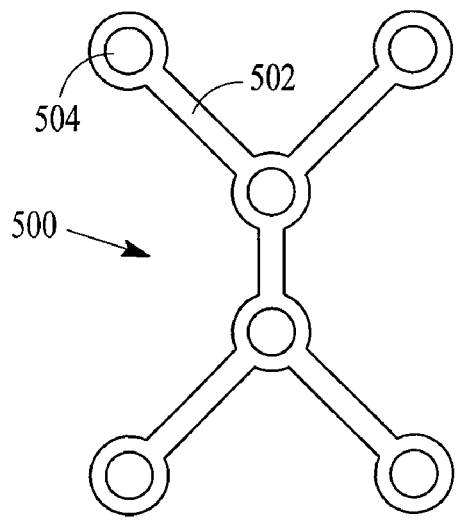
FIG. 5 illustrates an example bone support structure for use according to an embodiment of the invention.

FIG. 5 illustrates an example of a bone plate 500. As discussed above, bone plates 500 are included in the category of bone support structure, however additional bone support structures other than plates are included within the scope of the invention. Holes 504 are shown to accept polymer fasteners as described in embodiments above. Other plate portions 502 form structure between the holes 504.

Figure 6:
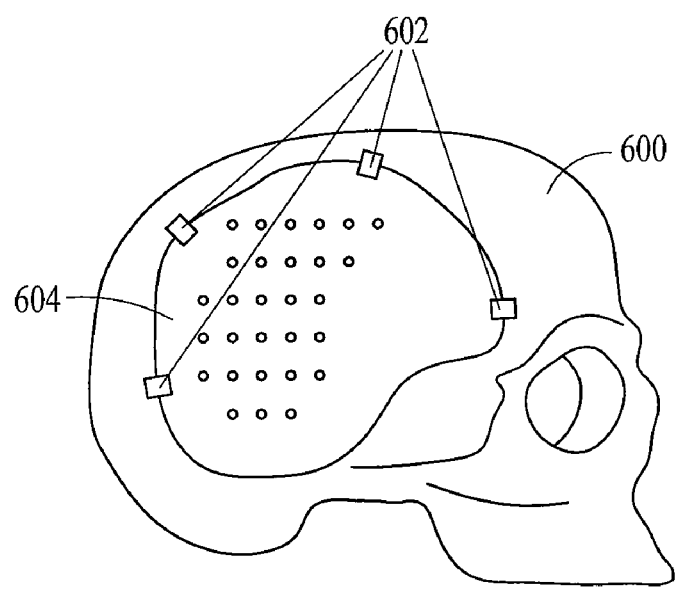
FIG. 6 illustrates a number of example bone support structures in place on a skull according to an embodiment of the invention.

FIG. 6 illustrates one example use of bone plates in conjunction with polymer fasteners as described in embodiments above. A skull 600 is used as an example portion of bone. A first plate 604 is shown secured to the skull 600 using a number of bone plates 602 and polymer fasteners as described in selected embodiments above.

Figure 7:
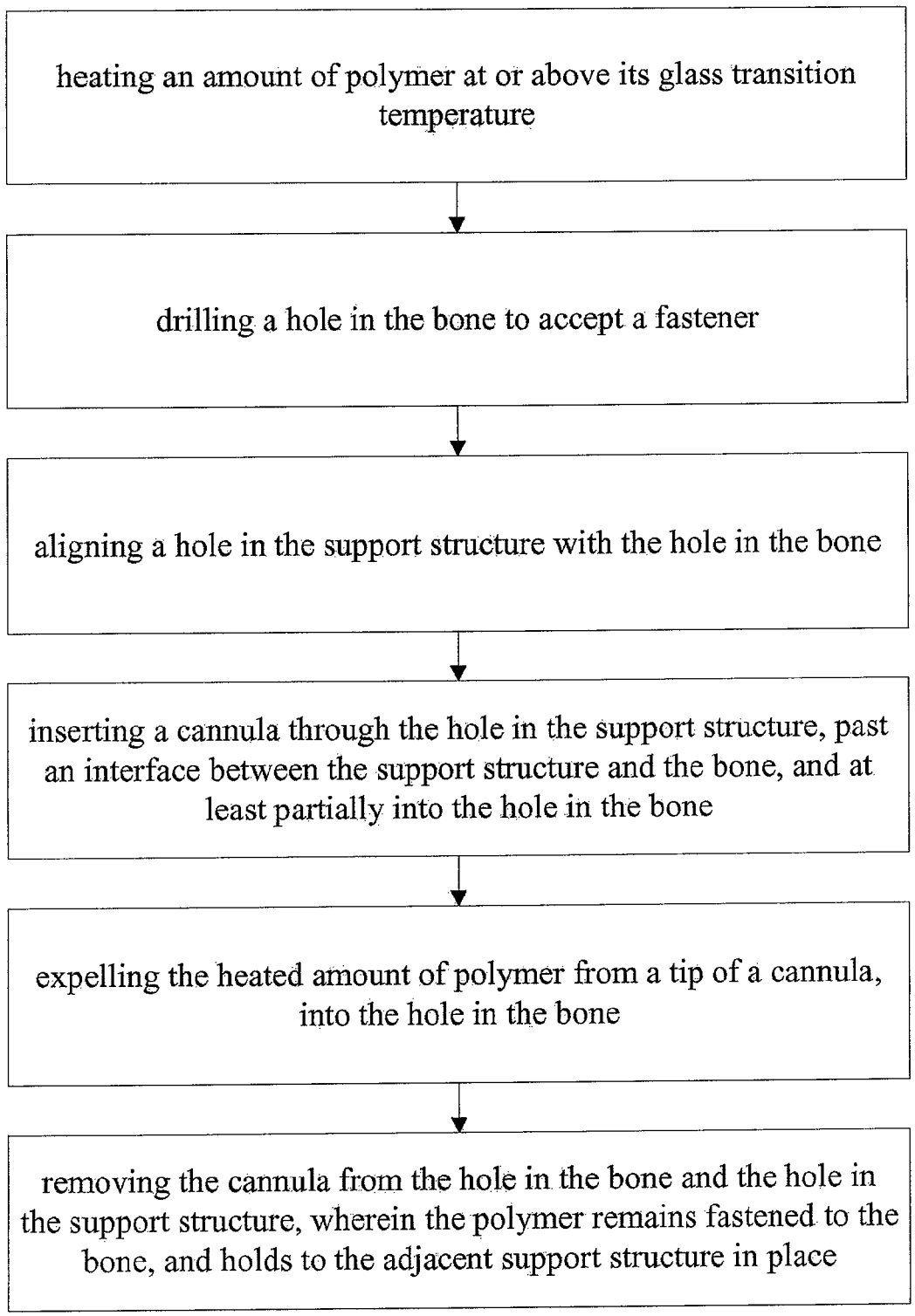
FIG. 7 is a flow diagram of an example method according to an embodiment of the invention.

FIG. 7 illustrates an example method according to an embodiment of the invention. An amount of polymer is heated heating to a temperature at or above its glass transition temperature. A hole is drilled in a bone to accept a fastener. The hole in the bone is aligned with a hole in a support structure, such as a bone plate. A cannula is inserted through the hole in the support structure, past an interface between the support structure and the bone, and at least partially into the hole in the bone. As discussed above, the insertion of the cannula to this location helps prevent extrusion of polymer at the interface. Insertion of the cannula further aids in alignment of the holes. The heated amount of polymer is then expelled from a tip of a cannula, into the hole in the bone, and the cannula is removed from the hole in the bone and the hole in the support structure. The polymer left in the holes forms a fastener, as described in selected embodiments above.

While a number of example embodiments and advantages of the invention are described, the above examples are not exhaustive, and are for illustration only. Although specific embodiments have been illustrated and described herein, it will be appreciated by those of ordinary skill in the art that any arrangement or method which is calculated to achieve the same purpose may be substituted for the specific embodiment shown. This application is intended to cover any adaptations or variations of the present invention. It is to be understood that the above description is intended to be illustrative, and not restrictive. Combinations of the above embodiments, and other embodiments will be apparent to those of skill in the art upon reviewing the above description. The scope of the invention includes any other applications in which the above structures and methods are used. The scope of the invention should be determined with reference to the appended claims, along with the full scope of equivalents to which such claims are entitled.

The Abstract is provided to comply with 37 C.F.R. §1.72(b) to allow the reader to quickly ascertain the nature and gist of the technical disclosure. The
Abstract is submitted with the understanding that it will not be used to interpret or limit the scope or meaning of the claims.

What is claimed is:

1. A bone support attachment device, comprising:
   an injection cannula sized to hold an amount of polymer to form a single fastener;
   a polymer supply inlet coupled to a side of the injection cannula;
   a plunger having a tip disposed at a first end of the injection cannula such that when actuated, the plunger cuts off the supply inlet and subsequently expels the amount of polymer from a second end of the injection cannula upon the plunger reaching the second end of the injection cannula;
   a chamber sized to house a block of polymer sufficient to form a plurality of fasteners, the chamber connected to the supply inlet to sequentially provide the amount of polymer to form a single fastener from a single chamber full of polymer; and
   an actively regulated heater configured to maintain a consistent temperature profile from the first end of the cannula to the second end of the cannula, wherein the temperature profile comprises a temperature gradient from the first end of the injection cannula to the second end of the injection cannula and wherein the temperature gradient is warmer at the first end of the injection cannula than at the second end of the injection cannula.

2. The bone support attachment device of claim 1, wherein a starting plunger location is variable to provide a variable volume in the injection cannula that corresponds to a selectable amount of polymer to form fasteners of various sizes.

3. The bone support attachment device of claim 1, wherein a temperature at the second end of the injection cannula is controlled in a range within approximately 37-55 degrees Centigrade.

4. The bone support attachment device of claim 1, further comprising a chamber plunger configured to expel polymer from the chamber into the injection cannula when actuated.

5. The bone support attachment device of claim 1, wherein the chamber is configured to receive a plurality of discrete polymer sections that are not heated in the chamber.

6. The bone support attachment device of claim 1, wherein at least a portion of the plunger is configured to reduce adhesion of polymer to the plunger.

7. The bone support attachment device of claim1, further comprising an actuator configured to advance the plunger at a rate sufficient for at least a portion of the polymer expelled from the cannula to interdigitate within a bone into which the injection cannula is extended.

8. The bone support attachment device of claim 1, further comprising an actuator configured to advance the plunger at a rate sufficient to form a bulbous polymer tip proximate a point distal to the second end of the injection cannula, the point distal to the second end of the injection cannula being defined by an inner cortical bone surface that is opposite a cortical bone surface upon which a bone support is positioned when the injection cannula is extended through the bone support during operation of the bone support attachment device.

9. The bone support attachment device of claim 1 wherein the actively regulated heater comprises multiple heating elements.

10. The bone support attachment device of claim 1 wherein the actively regulated heater comprises multiple thermal control circuits.

11. The bone support attachment device of claim 1 further comprising a depth gauge proximate a distal tip of the bone support attachment device, the depth gauge configured to move relative to the injection cannula once a predetermined volume of polymer is expelled from the injection cannula.

12. The bone support attachment device of claim 11, wherein the second end of the injection cannula is configured to extend a selectable distance from the depth gauge, the selectable distance being greater than a thickness of a bone support such that when the bone support is engaged with a static shelf of the depth gauge, the second end of the injection cannula extends completely through the bone support.

13. The bone support attachment device of claim 11, wherein the depth gauge is positionable at a selectable distance from the distal tip.

14. The bone support attachment device of claim 1 wherein the actively regulated heater is configured to raise the temperature of polymer within the injection cannula to the melting point of the polymer and is configured to actively control the temperature of polymer at the second end of the injection cannula to a temperature that is low enough to not cause necrosis when the polymer is discharged from the injection cannula to contact tissue.

15. The bone support attachment device of claim 1 wherein the actively regulated heater is configured to raise the temperature of polymer within the injection cannula to between 50° C. and 250° C.

16. The bone support attachment device of claim 15 wherein the actively regulated heater is configured to raise the temperature of polymer within the injection cannula to between 130° C. and 180° C.

* * * * *